US00PP34896P2

(12) United States Plant Patent
Hansen

(10) Patent No.: US PP34,896 P2
(45) Date of Patent: Jan. 3, 2023

(54) ***AGASTACHE* PLANT NAMED 'QUEEN NECTARINE'**

(50) Latin Name: ***Agastache* hybrid**
Varietal Denomination: Queen Nectarine

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/803,304

(22) Filed: Apr. 28, 2022

(51) Int. Cl.
*A01H 5/02* (2018.01)
*A01H 6/50* (2018.01)

(52) U.S. Cl.
USPC ..... Plt./399
CPC ..... *A01H 6/50* (2018.05)

(58) Field of Classification Search
USPC ..... Plt./384, 399
CPC ..... A01H 5/02
See application file for complete search history.

*Primary Examiner* — Kent L Bell

(57) ABSTRACT

A new and unique cultivar of hyssop, *Agastache* plant named 'Queen Nectarine' with medium-sized, dense, rounded, well-branched habit. The flowers cover the top two-thirds of the plant, are large, soft-peach colored, with mauve-colored calyxes in densely branched panicles over an extended period beginning in early summer. The new plant is useful in the landscape and as a cut flower.

1 Drawing Sheet

Botanical denomination: *Agastache* hybrid.
Variety designation: 'Queen Nectarine'.

STATEMENT REGARDING PRIOR DISCLOSURES UNDER 37 CFR 1.77(b)(6)

The first non-enabling disclosure of the claimed plant was made by Walters Gardens, Inc. on Dec. 1, 2021, in the form of a website brief description and photograph followed by a short description. The first enabling disclosure of a sales of the claimed plant was on May 17, 2021, by Walters Gardens, Inc to Casertano Greenhouses and Farms, Inc. Walters Gardens, Inc. obtained the new plant and information about the new plant directly from the inventor. No plants of *Agastache* 'Queen Nectarine' have been sold, in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct hyssop plant or anise hyssop from the genus *Agastache* and given the cultivar name 'Queen Nectarine'. The new plant was the result of a single seedling selection from a cross on Jul. 15, 2015, by the inventor between the proprietary, unreleased, hybrid, clone *Agastache* 11-28-1 (not patented) as the female or seed parent and the proprietary, unreleased, hybrid, clone *Agastache* HK10-18-50 (not patented) as the male or pollen parent. The seeds from the pollination were collected in the late summer of 2015. The individually selected seedling was eventually given the breeder code 15-5-21 after being first isolated from trials at a nursery in Zeeland, Mich. during the summer of 2017. It was selected for the final introduction in the summer of 2019.

*Agastache* 'Queen Nectarine' has been asexually propagated at the same nursery in Zeeland, Mich. originally by basal shoot cuttings followed by traditional shoot tip and stem cutting procedures and found to reproduce plants that are identical and exhibit all the characteristics of the original plant in successive generations of asexual propagation.

The new plant, *Agastache* 'Queen Nectarine', has not been observed under all possible environments. The phenotype may vary slightly with different environmental conditions, such as temperature, light, fertility, moisture and maturity levels, but without any change in the genotype.

In comparison to the new plant, the seed parent is slightly shorter and more open in habit range. The male parent has a different flower color and is more compact in habit.

The nearest comparison varieties known to the inventor are: 'Peachie Keen' U.S. Plant Pat. No. 25,886, 'Mango Tango' U.S. Plant Pat. No. 25,747, 'Kudos Coral' U.S. Plant Pat. No. 25,613, 'Kudos Mandarin' U.S. Plant Pat. No. 25,381 and 'Summer Sunset' U.S. Plant Pat. No. 23,623.

'Peachie Keen' has a smaller habit in both height and width, and with less heavily-branched panicles. 'Mango Tango' has a significantly shorter and more compact habit, and the flowers are vibrant mango-orange colored. 'Kudos Mandarin' has deeper orange-colored flowers with a significantly smaller habit. 'Kudos Coral' has a narrower and smaller habit in both height and width, and the flower is more reddish-colored. 'Summer Sunset' is less winter-hardy, smaller and narrower in habit, and the flower color contains more orangish coloration. Both 'Kudos Mandarin' and 'Kudos Coral' have not overwintered under similar conditions where the new plant has survived the winter.

The new plant *Agastache* 'Queen Nectarine' is distinct from the parents and all other anise hyssop known to the inventor in the following combined traits:

1. Medium-sized, dense, well-branched, rounded, full, habit;

2. Large flowers of soft-peach coloration in densely branched panicles;
3. Long bloom time with effectiveness extended by persistent, mauve-colored calyxes;
4. Foliage is dark green;
5. Flowers covering the upper two-thirds of the plant beginning in early summer to fall.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source and direction may cause the appearance of minor variation in color.

DETAILED PLANT DESCRIPTION

Figure 1:
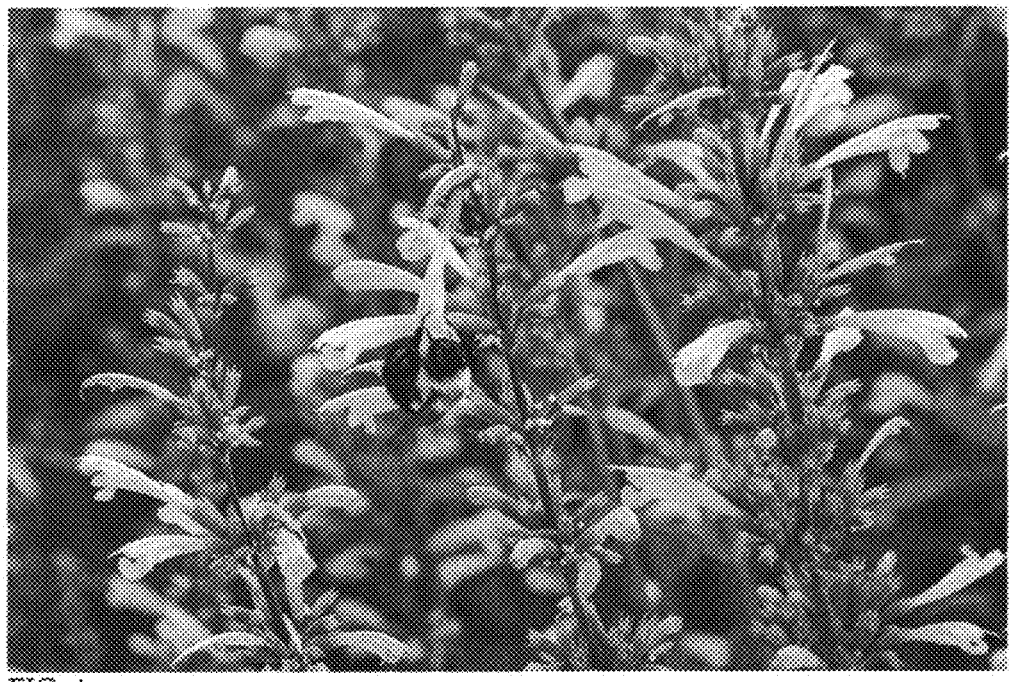
FIG. 1 shows a close-up of the scapes with flowers, buds and calyxes.
Figure 2:
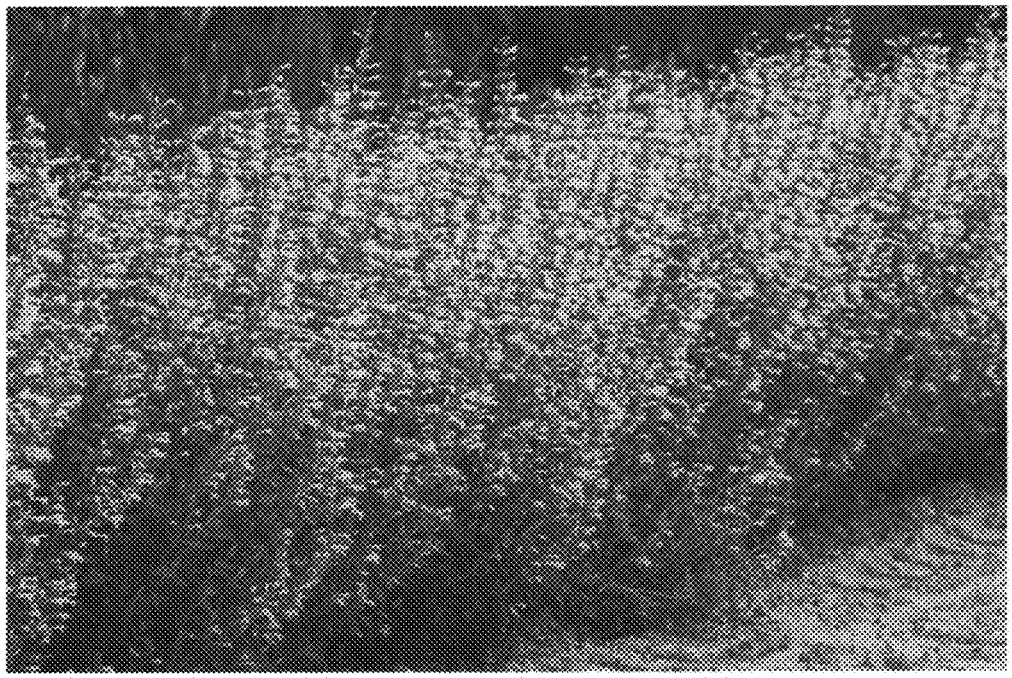
FIG. 2 shows a side view of two-year-old plants in mid-season flower in an overwintered trial block at a nursery near Zeeland, Mich.

The following is a detailed description of the new *Agastache* cultivar 'Queen Nectarine' based on observations of a three-year-old specimen grown with supplemental watering and fertilizer as needed in a display garden at a wholesale perennial nursery in Zeeland, Mich. Color descriptions are from the 2015 edition of The Royal Horticultural Society Colour Chart except where common dictionary terms are used.

Plant habit: Multi-stemmed herbaceous perennial, rounded, heavily branched;

Plant size: Without growth retardants or pinching—to about 92 cm tall and 110 cm across;

Roots: Fibrous, well-branched; to about 2 mm diameter near base; color light tan nearest RHS 165D depending on soil type;

Stem: Quadrangular; fistulous; stiff; wiry; finely pubescent; to about 6 mm across at base and 60 cm tall with flowering starting about 35 cm above soil; ten internodes below branched peduncle; internodes average about 3.5 cm long; about eight to ten stems per plant;

Primary branches: Quadrate; opposite; about ten per plant; to about 49 cm long and about 4 mm diameter at base;

Secondary branches: Quadrangular; opposite; up to six per primary branch; to about 40 cm long and 2.5 mm diameter at base;

Primary and secondary branch color: Proximal portions nearest RHS 146C, distal portions nearest RHS 146B; nodes nearest RHS 194A;

Leaf: Simple; opposite; broadly lanceolate, base truncate; apex acute; margin serrate with seven to ten teeth per side; adaxial and abaxial surfaces glabrous and matte;

Leaf size: To about 46 mm long and 16 mm across at base, decreasing distally;

Leaf venation: Reticulate; glabrous and slightly impressed adaxial, puberulent and costate abaxial;

Leaf color: Young expanding adaxial between RHS 146A and RHS 137A, abaxial between RHS N77D and N77C with distal edge with undertone of nearest RHS 137A; mature adaxial nearest RHS 137B and abaxial nearest RHS 147B;

Vein color: Adaxial nearest RHS 151D, abaxial midrib nearest RHS 148C and secondary veins between RHS N77C and RHS N77D;

Leaf fragrance: Moderately herbal, minty;

Petiole: Micro-puberulent adaxial and abaxial; deeply concave-convex; to 8 mm long and 2 mm across, average 6 mm long and 1.5 mm;

Petiole color: Adaxial nearest RHS 147B with a light blush of nearest RHS N77D; abaxial nearest RHS 146D;

Inflorescence: In densely branched panicle with short branches or whorls in axils; 8 to 60 flowers on two short branchlets per node; up to 12 nodes per main stem, and 2,000 to 3,000 flowers per main stem; terminal flowering portion about 24 cm long and about 7.5 cm across; total flowering portion about 42 cm long and about 38 cm across; each stem flowering for about 5 weeks but remain effective for about 6 weeks or more because of the strongly pigmented persistent calyxes; repeating if deadheaded;

Bloom period: Early July through frost in Zeeland, Mich.;

Peduncle: Average about 62 cm tall and about 5 mm at base; puberulent; attitude upward;

Peduncle color: Nearest RHS 146B with distal portion light to heavily blushed with nearest RHS 186C;

Pedicel: Cylindrical; short; glabrous; matte; to about 2 mm long and 0.5 mm diameter; altitude mostly upright; color nearest RHS 182A;

Flower: Perfect; complete; zygomorphic; sympetalous; bilabiate, with five united petals forming an upper lip 2-lobed and lower lip 3-lobed; attitude outwardly to slightly upwardly;

Flower size: About 30 mm long to exerted stamens and style, about 9 mm tall and 7.5 mm across; corolla to about 24 mm long, 6 mm tall, and 5 mm across, about 3 mm diameter at fusion of two lips;

Flower period: Individual flowers open for about 3 days; individual panicle lasting for about 5 weeks but remain effective for about 6 weeks and entire plant flowering from early summer to fall;

Bud on day prior to opening: Arcuate; clavate to obelliptical; about 25 mm long, 5.5 mm tall and 3 mm wide just before the apex and 1.5 mm wide at base;

Bud color: Petals nearest RHS 25B toward apex, ventral portion nearest RHS 20A, dorsal portion between RHS 22B and RHS 21C, ventral base nearest RHS 20A and dorsal base between RHS 22B and RHS 21C; calyx nearest RHS N77B with veins nearest RHS N79B;

Petals: Micro-puberulent outside, glabrous inside; matte both adaxial and abaxial; upper and lower petals proximally fused forming tube in the basal 20 mm;

Upper 2-lobed petal: About 26 mm long and 6 mm across toward apex; lobes centrally cleft about 1.5 mm deep; lobe apices rounded; margin entire;

Lower 3-lobed petal: About 25 mm long, 3.5 mm wide at fusion and 7.5 mm across near middle; arcuate downward in distal 6 mm; center lobe about 4 mm long and 4 mm across, with a rounded emarginate apex 1 mm deep and crenate margin; two side lobes of lower petal spread horizontally, about 2 mm long and 2 mm wide, with rounded apex and entire margin;

Petal color: Abaxial and adaxial upper labium nearest RHS 23D, lower labium adaxial apical portion nearest RHS 23B, proximal portion nearest RHS 23C, lower labium abaxial nearest RHS 23C; corolla tube adaxial and abaxial basal throat portion nearest RHS 25D, and adaxial and abaxial distal corolla tube throat nearest RHS 27D; color not changing with maturity;

Calyx: Entire; about 7 mm long and diameter about 2.5 mm;

Sepals: Five; linear; acute apices; entire margin; fused into tube in basal 6 mm; puberulent outside and glabrous inside; to about 7 mm long, and 1 mm across at fusion;

Calyx color: Adaxial nearest RHS 146C with veins nearest RHS 146A and apex strongly blushed with RHS 64B; abaxial nearest RHS 148B with moderate to strong blush of nearest RHS 64B concentrated distally to solid RHS 64B at apex;

Gynoecium: Single; to 30 mm long; exerted;

*Style*.—One, about 29 mm long and about 0.3 mm diameter; terete; glabrous; straight; translucent; color distal 5 to 7 mm nearest RHS 24D, proximally nearest RHS 8D.

*Stigma*.—Bifid and reflex; each segment about 1 mm long and about 0.3 mm diameter; tapering to a pointed apex; color nearest RHS 59B.

*Ovary*.—Superior; about 0.5 mm diameter.

*Ovary color*.—Between RHS 150D and RHS 150C.

Androecium:

*Stamen*.—In two sets of two, exerted, adnate to the inner corolla.

*Filaments*.—Two longer and two shorter; paired and exerted; longer pair adnate in the basal 21 mm and free in the proximal 9 mm; shorter pair adnate in the basal 15 mm and free in the proximal 9 mm; color nearest RHS 29C.

*Anthers*.—Dorsifixed; versatile; folded; longitudinal; about 1.2 mm long and about 0.8 mm across; color nearest RHS 72A.

*Pollen*.—Abundant; color nearest RHS NN155A.

Fragrance: None detected;

Fruit: Two carpels;

Seed: Nutlet, typically one to two per naturally pollinated flower, ellipsoidal; about 1 mm long, 0.8 mm across and 0.5 mm thick;

Seed color: Nearest 202A;

Resistance: 'Queen Nectarine' is resistant to *Odocoileus hemionus* browsing, and shows no susceptibility to Downy Mildew (*Perononspora*) but has not been tested or shown resistance to other pests and diseases common to *Agastache*.

Hardiness: The new plant has survived USDA hardiness zones 6 to 10 but has not been tested yet beyond these temperatures.

The invention claimed is:

1. A new and distinct cultivar of *Agastache* plant named 'Queen Nectarine' as herein described and illustrated.

* * * * *